US00PP23855P3

(12) United States Plant Patent
Korlipara

(10) Patent No.: US PP23,855 P3
(45) Date of Patent: Aug. 27, 2013

(54) ***NEPETA* PLANT NAMED 'BLUE LAGOON'**

(50) Latin Name: ***Nepeta* spp.**
Varietal Denomination: Blue Lagoon

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 162 days.

(21) Appl. No.: 13/373,272

(22) Filed: Nov. 8, 2011

(65) Prior Publication Data

US 2013/0117898 P1 May 9, 2013

(51) Int. Cl.
*A01H 5/00* (2006.01)

(52) U.S. Cl.
USPC ..... Plt./263.1

(58) Field of Classification Search
USPC ..... Plt./263.1, 258
See application file for complete search history.

*Primary Examiner* — Howard Locker
(74) *Attorney, Agent, or Firm* — Klarquist Sparkman, LLP

(57) ABSTRACT

A new and distinct form of *Nepeta* plant characterized by a low, dense habit, an excellent crowns count, clean-looking, green, lemon-scented foliage, and excellent vigor.

1 Drawing Sheet

Botanical denomination: *Nepeta* spp.
Variety designation: 'Blue Lagoon'.

BACKGROUND OF THE INVENTION

The present invention relates to a new and distinct cultivar of *Nepeta*, given the name, 'Blue Lagoon'. *Nepeta* is in the family Lamiaceae. This plant originated from a planned breeding cross between *Nepeta racemosa*, as the seed parent, and *Nepeta cataria* 'Citriodora', as the pollen parent. This cultivar was selected for its low growing habit, long flowering time, short, dense, purple blue inflorescences on dark peduncles, and clean attractive look. It is an ideal plant for a sunny border.

Compared to the seed parent, *Nepeta racemosa*, an unpatented plant, the new cultivar has shorter, darker inflorescences with a dark rather than a green flowering stem and a lower denser habit.

Compared to the pollen parent, *Nepeta cataria* 'Citriodora', an unpatented plant, the new cultivar has shorter darker inflorescences and darker green leaves.

*Nepeta* 'Blue Lagoon' is uniquely distinguished by:

1. a low, dense habit,
2. excellent crowns count,
3. clean-looking, green, lemon-scented foliage, and
4. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of a one-year-old *Nepeta* 'Blue Lagoon' growing in a two gallon container in May in Canby, Oreg.

FIG. 2 shows a two-year-old *Nepeta* 'Blue Lagoon' growing in the ground in the trial beds in full sun in June in Canby, Oreg.

DETAILED PLANT DESCRIPTION

The following is a detailed description of the new *Nepeta* cultivar based on observations of a two-year-old specimen grown outside in two gallon containers in Canby, Oreg. in May. The color descriptions are all based on The Royal Horticultural Society Colour Chart, 5$^{th}$ edition.

Plant:

*Type*.—Herbaceous perennial.
*Form*.—Procumbent, clumping ground cover.
*Cold hardiness*.—USDA Zone 6-10.
*Size*.—Grows to 60 cm wide and 12 cm high.
*Vigor*.—Excellent.
*Stem number*.—About 60 stems from the crown.
*Stem*.—Branching from every node, grows to 17 cm long and 3 mm wide (at the base), internodes grow to 2 cm long, pubescent, Greyed Orange 166A, square in cross section.
*Rooting*.—Plants root easily from stem cuttings.

Leaf:

*Type*.—Simple, aromatic, lemon scented.
*Arrangement*.—Opposite.
*Shape*.—Ovate.
*Venation*.—Pinnate.
*Margins*.—Crenate.
*Apex*.—Obtuse.
*Base*.—Auriculate to cordate.
*Blade size*.—Grows to 3 cm long and 2.5 cm wide.
*Surface texture*.—Rugose, pubescent on both sides.
*Petiole*.—Grows to 7 mm, pubescent, Greyed Purple 183B.
*Leaf color*.—Topside Green 137B, bottom side Yellow Green 147B tinted Greyed Purple 187A.

Inflorescence:

*Type*.—Terminal many flowered dense verticillasters in opposite stalked to sessile cymes.

*Number of flowers*.—Opposite cymes in up to 12 rings of 5 to 20 flowers per cyme.

*Size of inflorescence*.—Grows to 6 cm long and 3.3 cm wide.

*Peduncle*.—Grows to 2 cm long and 2 mm wide, pubescent, Greyed Orange 166A.

*Pedicel*.—Sessile.

*Bloom period*.—May to October in Canby, Oreg.

Flower bud:

*Size*.—10 mm long and 3 mm wide at the widest point prior to opening.

*Description*.—Tubular.

*Surface texture*.—Pubescent.

*Color*.—Violet 85A.

Flower:

*Type*.—Zygomorphic.

*Shape*.—Bilabiate.

*Corolla description*.—13 mm long and to 11 mm wide; pubescent outside and glabrous inside; tube 8 mm long and Violet N88B at the top to 91D at the base; throat Violet N88B on outside, inside Violet 91A spotted Violet Blue 90A, 3 mm long and 4 mm wide, flattened dorsally; upper lip 3.5 mm wide and 3 mm long, two lobed, reflexed, Violet Blue 90A inside and out; lower lip 6 mm wide and 5 mm long, slightly cupped, 2 lobed, Violet Blue 90A, lateral lobes Violet Blue 90A and 2 mm long and 1 mm wide.

*Calyx description*.—Tubular, 5 lobed, 7 mm long and 2 mm wide, lobes narrow, tips acuminate, margin entire, villous outside, glabrous inside, Violet 83A.

*Pistil description*.—1, 12 mm long, ovary 1 mm long and Yellow Green 148A; style 10 mm long, Violet N88C at base to Violet 83A at stigma, stigma 1 mm long, Violet 83A.

*Stamen description*.—4, filaments 4 mm long and Violet 83A, anthers 1 mm long and Violet Blue N89A, pollen White NN155A.

*Fragrance*.—None.

*Lastingness*.—A spike blooms for about 6 weeks on the plant.

Fruit and seed: None seen.

Pests and diseases: No resistances are known. The new cultivar has shown no problems in Canby, Oreg.

I claim:

1. A new and distinct form of *Nepeta* plant substantially as shown and described.

* * * * *

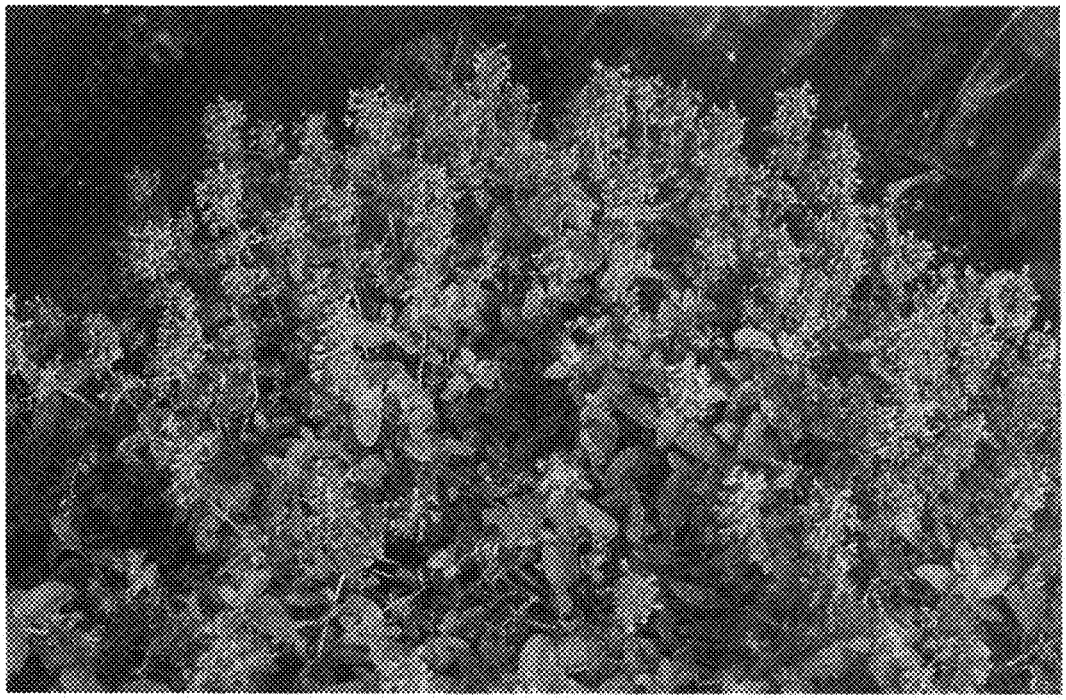

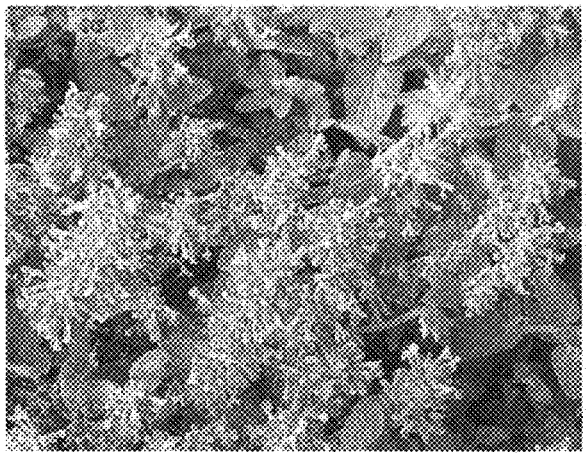
FIG. 1 above, FIG. 2 below